United States Patent
Tockman et al.

(10) Patent No.: US 10,265,097 B2
(45) Date of Patent: Apr. 23, 2019

(54) NEEDLE ASSEMBLY WITH RETRACTABLE CUTTING EDGE

(71) Applicant: Cardiac Pacemakers, Inc., St. Paul, MN (US)

(72) Inventors: Bruce A. Tockman, Scandia, MN (US); Brian Soltis, St. Paul, MN (US); Eric F. Hammill, Ham Lake, MN (US); Lili Liu, Maple Grove, MN (US); Juan Gabriel Hincapie Ordonez, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 677 days.

(21) Appl. No.: 14/865,983

(22) Filed: Sep. 25, 2015

(65) Prior Publication Data
US 2016/0089183 A1 Mar. 31, 2016

Related U.S. Application Data

(60) Provisional application No. 62/055,207, filed on Sep. 25, 2014.

(51) Int. Cl.
*A61B 17/34* (2006.01)
*A61N 1/05* (2006.01)
(Continued)

(52) U.S. Cl.
CPC ...... *A61B 17/3468* (2013.01); *A61B 17/3403* (2013.01); *A61N 1/0551* (2013.01);
(Continued)

(58) Field of Classification Search
CPC ............ A61B 17/3468; A61B 17/3403; A61N 1/0551; A61N 1/36053
See application file for complete search history.

(56) References Cited

U.S. PATENT DOCUMENTS

| | | | |
|---|---|---|---|
| 4,285,347 A | 8/1981 | Hess | |
| 5,026,350 A * | 6/1991 | Tanaka | A61M 5/32 604/158 |

(Continued)

FOREIGN PATENT DOCUMENTS

WO 2013179006 A1 12/2013

OTHER PUBLICATIONS

Su, Ching-luan et al., "A Study of Hydrophobic Electrospun Membrane Applied in Seawater Desalination by Membrane Distillation," Fibers and Polymers (2012), vol. 13, No. 6, pp. 698-702. DOI 10.1007/s12221-012-0698-3.

*Primary Examiner* — Tse W Chen
*Assistant Examiner* — Joanne M Hoffman (57) ABSTRACT

The disclosure relates to a needle assembly for delivering a lead and methods of use. The needle assembly is configured to cut tissue and reduce the potential for cutting vulnerable bodily structures. The needle assembly includes an outer needle with a blunt tip and an inner needle with a sharp tip. The outer needle may be curved, and the inner needle may be curved. When the inner needle is rotated with respect to the outer needle, the inner needle protracts or retracts with respect to the outer needle. A stopping feature on the needle assembly may be included to resist over-rotation or over-extension. The needle assembly provides an initial path that may be further dilated for delivering a lead, such as a vagus nerve stimulation lead to a target site. The target site may be electrically tested with some embodiments.

13 Claims, 9 Drawing Sheets

(51) Int. Cl.
*A61N 1/36* (2006.01)
*A61B 5/053* (2006.01)
*A61B 17/32* (2006.01)

(52) U.S. Cl.
CPC ........ *A61N 1/36053* (2013.01); *A61B 5/0538* (2013.01); *A61B 2017/320056* (2013.01); *A61B 2017/3413* (2013.01)

(56) References Cited

U.S. PATENT DOCUMENTS

| | | | |
|---|---|---|---|
| 5,292,310 A * | 3/1994 | Yoon | A61B 10/06 600/566 |
| 5,403,296 A * | 4/1995 | Mohring | A61M 25/065 604/158 |
| 5,591,138 A * | 1/1997 | Vaillancourt | A61M 5/3271 604/192 |
| 5,665,072 A * | 9/1997 | Yoon | A61B 17/3417 604/164.12 |
| 6,104,960 A * | 8/2000 | Duysens | A61N 1/0551 607/117 |
| 6,512,958 B1 | 1/2003 | Swoyer et al. | |
| 6,626,868 B1 * | 9/2003 | Prestidge | A61M 25/0631 604/158 |
| 6,847,849 B2 | 1/2005 | Mamo et al. | |
| 7,789,833 B2 | 9/2010 | Urbano et al. | |
| 7,941,227 B2 | 5/2011 | Barker | |
| 8,014,873 B2 | 9/2011 | Jones et al. | |
| 8,032,220 B2 | 10/2011 | Kuzma | |
| 8,532,793 B2 | 9/2013 | Morris et al. | |
| 2002/0151847 A1 * | 10/2002 | Takagi | A61M 25/0631 604/164.12 |
| 2003/0028147 A1 * | 2/2003 | Aves | A61B 17/3401 604/164.06 |
| 2005/0101984 A1 * | 5/2005 | Chanduszko | A61B 17/0057 606/185 |
| 2005/0113901 A1 * | 5/2005 | Coe | A61B 17/0469 607/130 |
| 2005/0149067 A1 * | 7/2005 | Takemoto | A61B 17/0467 606/144 |
| 2006/0025720 A1 * | 2/2006 | Sawa | A61M 25/0084 604/164.01 |
| 2006/0064062 A1 * | 3/2006 | Gurusamy | A61M 25/065 604/170.03 |
| 2007/0021767 A1 * | 1/2007 | Breznock | A61B 17/00234 606/185 |
| 2007/0032820 A1 * | 2/2007 | Chin-Chen | A61B 17/0057 606/213 |
| 2008/0215001 A1 * | 9/2008 | Cowe | A61M 5/326 604/110 |
| 2009/0112119 A1 * | 4/2009 | Kim | A61B 10/0266 600/564 |
| 2009/0157091 A1 * | 6/2009 | Buysman | A61N 1/0551 606/129 |
| 2009/0187116 A1 * | 7/2009 | Noishiki | A61B 10/025 600/564 |
| 2010/0094143 A1 * | 4/2010 | Mahapatra | A61B 5/4887 600/486 |
| 2010/0114140 A1 * | 5/2010 | Chanduszko | A61B 17/0057 606/185 |
| 2010/0331883 A1 * | 12/2010 | Schmitz | A61B 10/0275 606/249 |
| 2011/0270191 A1 * | 11/2011 | Paul | A61B 17/3478 604/164.1 |
| 2011/0319758 A1 * | 12/2011 | Wang | A61B 17/3403 600/439 |
| 2013/0197615 A1 | 8/2013 | Rundle et al. | |
| 2013/0310823 A1 * | 11/2013 | Gelfand | A61B 18/1492 606/33 |
| 2015/0011820 A1 * | 1/2015 | Kawaura | A61B 17/0482 600/30 |
| 2015/0073465 A1 * | 3/2015 | Ariura | A61B 5/6885 606/185 |
| 2015/0100099 A1 * | 4/2015 | Kitagawa | A61B 17/3403 606/86 A |
| 2015/0142040 A1 * | 5/2015 | Kawaura | A61B 17/06109 606/185 |
| 2018/0085142 A1 * | 3/2018 | Leeflang | A61B 17/00234 |

* cited by examiner

NEEDLE ASSEMBLY WITH RETRACTABLE CUTTING EDGE

CROSS-REFERENCE TO RELATED APPLICATION

This application claims priority to Provisional Application No. 62/055,207, filed Sep. 25, 2014, which is herein incorporated by reference in its entirety.

TECHNICAL FIELD

The present disclosure relates to medical devices and methods for delivering a lead. More specifically, the invention relates to devices and methods for tunneling and delivering a stimulation lead to a target site within the body.

BACKGROUND

The use of nerve stimulation for treating and controlling a variety of medical, psychiatric, and neurological disorders has seen significant growth over the last several decades, including for treatment of heart conditions, epilepsy, obesity, inflammatory disorders, and breathing disorders, among others. For example, modulation of the automatic balance with neural stimulation has been shown to be possible and have positive clinical benefits, such as protecting the myocardium from further remodeling and predisposition to arrhythmias following a myocardial infarction (MI). Nerve stimulation can be accomplished with invasive surgical placement of a stimulating electrode adjacent to the vagus nerve. There remains a continuing need for percutaneous tools and methods for more effectively tunneling through tissue and delivering stimulation leads to the target site surrounded by vulnerable structures.

SUMMARY

According to Example 1, a needle assembly comprises an outer needle including a proximal end having a proximal opening, a distal end having a distal opening, a shaft defining a lumen extending between the proximal opening and the distal opening, and a tip on the distal end, the distal end extending in a non-linear path relative to the shaft; and an inner needle including a proximal end, a distal end, a shaft extending between the proximal end and the distal end, and a tip on the distal end adapted to cut tissue, the distal end extending in a non-linear path relative to the shaft, the inner needle removably received into the lumen of the outer needle shaft. The needle assembly is configured to be transitioned between a protracted position and a retracted position. In the protracted position, the tip of the inner needle extends outwardly from the distal opening of the outer needle to facilitate cutting tissue, and in the retracted position, the tip of the inner needle is positioned within the distal opening of the outer needle so that the tip of the inner needle is not directly exposed to tissue as the needle assembly is advanced therethrough in use.

Example 2 includes the needle assembly according to Example 1, wherein the distal end of the inner needle is curved relative to the shaft of the inner needle, and wherein the distal end of the outer needle is curved relative to the shaft of the outer needle.

Example 3 includes the needle assembly according to Examples 1 or 2, wherein the distal ends of the inner and outer needles have curvatures configured so that the distal end of the outer needle receives the distal end of the inner needle in a nesting fit when the inner needle is in the retracted position.

Example 4 includes the needle assembly of according to any of Examples 1-3, wherein the needle assembly is configured such that the inner needle transitions from the retracted position to the protracted position in response to a first rotation of the inner needle relative to the outer needle and transitions from the protracted position to the retracted position in response to a second rotation relative to the outer needle, and wherein the tip of the inner needle has a first orientation in the retracted position and a second orientation, which is opposite the first orientation, in the protracted position.

Example 5 includes the needle assembly according to any of Examples 1-4, wherein the inner needle is configured to be releasably locked in the protracted position.

Example 6 includes the needle assembly according to any of Examples 1-5, wherein the distal ends of the inner and outer needles have complementary curvatures configured to cooperate so as to releasably retain the inner needle in the protracted position.

Example 7 includes the needle assembly according to any of Examples 1-6, further including one or more threads disposed on the outer needle and the inner needle configured to cooperatively guide the movement of the inner needle between the protracted position and the retracted position upon relative rotation of the inner and outer needles.

Example 8 includes the needle assembly according to any of Examples 1-7, further including a first stopping feature on one or both of the outer needle and the inner needle configured to inhibit extension of the inner needle beyond the protracted position.

Example 9 includes the needle assembly according to any of Examples 4-8, further including a second stopping feature configured to inhibit rotation of the inner needle relative to the outer needle beyond the second orientation.

Example 10 includes needle assembly according to any of Examples 1-9, wherein the tip of the inner needle comprises one of a point, a bevel tip, and a bevel edge extending along a length of the inner needle.

Example 11 includes the needle assembly according to any of Examples 1-10, wherein the inner needle includes a handle on the proximal end having a dimension greater than a diameter of the proximal opening of the outer needle so as to operate as an extension stop for the inner needle.

Example 12 includes the needle assembly according to any of Examples 1-11, wherein the inner needle and the lumen of the outer needle have diameters sized so that the inner needle can slidably contact an inner surface of the lumen when the inner needle is disposed within the lumen.

Example 13 includes the needle assembly according to any of Examples 1-12, wherein the inner needle and the outer needle are each at least partially made of an electrically conductive material, and wherein the distal end of the outer needle is electrically coupled to the proximal end of the inner needle through contact between the inner needle and an inner surface of the lumen of the outer needle, and further including a conductive wire electrically coupled to the proximal end of the inner needle for conducting an electrical stimulation pulse to the inner needle.

Example 14 includes the needle assembly according to any of Examples 1-13, further including an insulator on the shaft of the outer needle.

Example 15 includes the needle assembly according to any of Examples 1-14, wherein the inner needle and the lumen of the outer needle are sized to provide a close fit therebetween to inhibit take up of tissue into the lumen of the outer needle as the needle assembly is advanced through the tissue.

According to Example 16, a needle assembly comprises an outer needle including a proximal end having a proximal opening, a distal end having a distal opening, a shaft defining a lumen extending between the proximal opening and the distal opening, and a tip on the distal end, the distal end being curved relative to the shaft; and an inner needle including a proximal end, a distal end, a shaft extending between the proximal end and the distal end, and a tip on the distal end adapted to cut tissue, the distal end being curved relative to the shaft, the inner needle removably received into the lumen. The needle assembly is configured to be transitioned between a protracted position and a retracted position. In the protracted position, the tip of the inner needle extends outwardly from the distal opening of the outer needle to facilitate cutting tissue, and in the retracted position, the tip of the inner needle is positioned within the distal opening of the outer needle so that the tip of the inner needle is not directly exposed to tissue as the needle assembly is advanced therethrough in use. The curvatures of the distal ends of the inner and outer needles are configured so that the distal end of the outer needle receives the distal end of the inner needle in a nesting fit when the inner needle is in the retracted position, and are configured further so that the inner needle transitions from the retracted position to the protracted position in response to a first rotation relative to the outer needle.

Example 17 includes the needle assembly according to Example 16, wherein the needle assembly is configured such that the inner needle transitions from the protracted position to the retracted position in response to a second rotation relative to the outer needle, and wherein the tip of the inner needle has a first orientation in the retracted position and a second orientation, which is opposite the first orientation, in the protracted position.

Example 18 includes the needle assembly according to Example 16, wherein the inner needle is configured to be releasably locked in the protracted position.

Example 19 includes the needle assembly according to Example 18, wherein the distal ends of the inner and outer needles have complementary curvatures configured to cooperate so as to releasably retain the inner needle in the protracted position.

Example 20 includes the needle assembly according to Example 19, further including one or more threads disposed on the outer needle and the inner needle configured to cooperatively guide the movement of the inner needle between the protracted position and the retracted position upon relative rotation of the inner and outer needles.

Example 21 includes the needle assembly according to Example 19, further including a first stopping feature on one or both of the outer needle and the inner needle configured to inhibit extension of the inner needle beyond the protracted position.

Example 22 includes the needle assembly according to Example 21, further including a second stopping feature configured to inhibit rotation of the inner needle relative to the outer needle beyond the second orientation.

Example 23 includes the needle assembly according to Example 16, wherein the inner needle and the lumen of the outer needle have diameters sized so that the inner needle can slidably contact an inner surface of the lumen when the inner needle is disposed within the lumen.

Example 24 includes the needle assembly according to Example 23, wherein the inner needle and the outer needle are each at least partially made of an electrically conductive material, and wherein the distal end of the outer needle is electrically coupled to the proximal end of the inner needle through contact between the inner needle and an inner surface of the lumen of the outer needle, and further including a conductive wire electrically coupled to the proximal end of the inner needle for conducting an electrical stimulation pulse to the inner needle.

Example 25 includes the needle assembly according to Example 24, further including an insulator on the shaft of the outer needle proximal to the distal end thereof.

Example 26 includes the needle assembly according to Example 25, wherein the inner needle and the lumen of the outer needle are sized to provide a close fit therebetween to inhibit take up of tissue into the lumen of the outer needle as the needle assembly is advanced through the tissue.

According to Example 27, a needle assembly comprises an outer needle including a proximal end having a proximal opening, a distal end having a distal opening, a shaft defining a lumen extending between the proximal opening and the distal opening, and a tip on the distal end, the distal end extending in a non-linear path relative to the shaft; and an inner needle including a proximal end, a distal end, a shaft extending between the proximal end and the distal end, and a tip on the distal end adapted to cut tissue, the distal end extending in a non-linear path relative to the shaft, the inner needle removably received into the lumen. The needle assembly is configured to be transitioned between a protracted position and a retracted position. In the protracted position, the tip of the inner needle extends outwardly from the distal opening of the outer needle to facilitate cutting tissue, and in the retracted position, the tip of the inner needle is positioned within the distal opening of the outer needle so that the tip of the inner needle is not directly exposed to tissue as the needle assembly is advanced therethrough in use. The shapes of the distal ends of the inner and outer needles are configured so that the distal end of the outer needle receives the distal end of the inner needle in a nesting fit when the inner needle is in the retracted position, and are configured further so that the inner needle transitions from the retracted position to the protracted position in response to a first rotation relative to the outer needle.

Example 28 includes the needle assembly according to Example 27, wherein the inner needle is configured to be releasably locked in the protracted position, and wherein the needle assembly is further configured so that the inner needle transitions from the protracted position to the retracted position in response to a second rotation relative to the outer needle.

According to Example 29, a method of tunneling to a target site in a body having tissue comprises: advancing a needle assembly subcutaneously through tissue toward the target site, the needle assembly including an outer needle and an inner needle, the inner needle removably disposed within a lumen of the outer needle, a tip of the inner needle being protracted extending outwardly from a tip of the outer needle; determining whether the needle assembly is approaching a bodily structure near the target site; rotating the inner needle relative to the outer needle to cause the inner needle to assume a retracted position, wherein the tip of the inner needle is nested within a distal end of the outer needle and not exposed to the tissue; and further advancing the needle assembly subcutaneously to the target site with the inner needle in the retracted position.

Example 30 includes the method according to Example 29, wherein advancing the needle assembly is conducted under ultrasonic imaging guidance.

Example 31 includes the method according to Example 30, further including testing the target site electrically with the tip of the outer needle.

Example 32 includes the method according to Example 31, further including removing the inner needle from the outer needle in response to the testing.

Example 33 includes the method according to Example 32, further including advancing a guidewire through the outer needle toward the target site after removing the inner needle.

Example 34 includes the method according to Example 33, further including removing the outer needle from the body.

Example 35 includes the method according to Example 34, further including: advancing a sheath assembly over the guide wire toward the test site; and advancing a lead through the sheath assembly.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
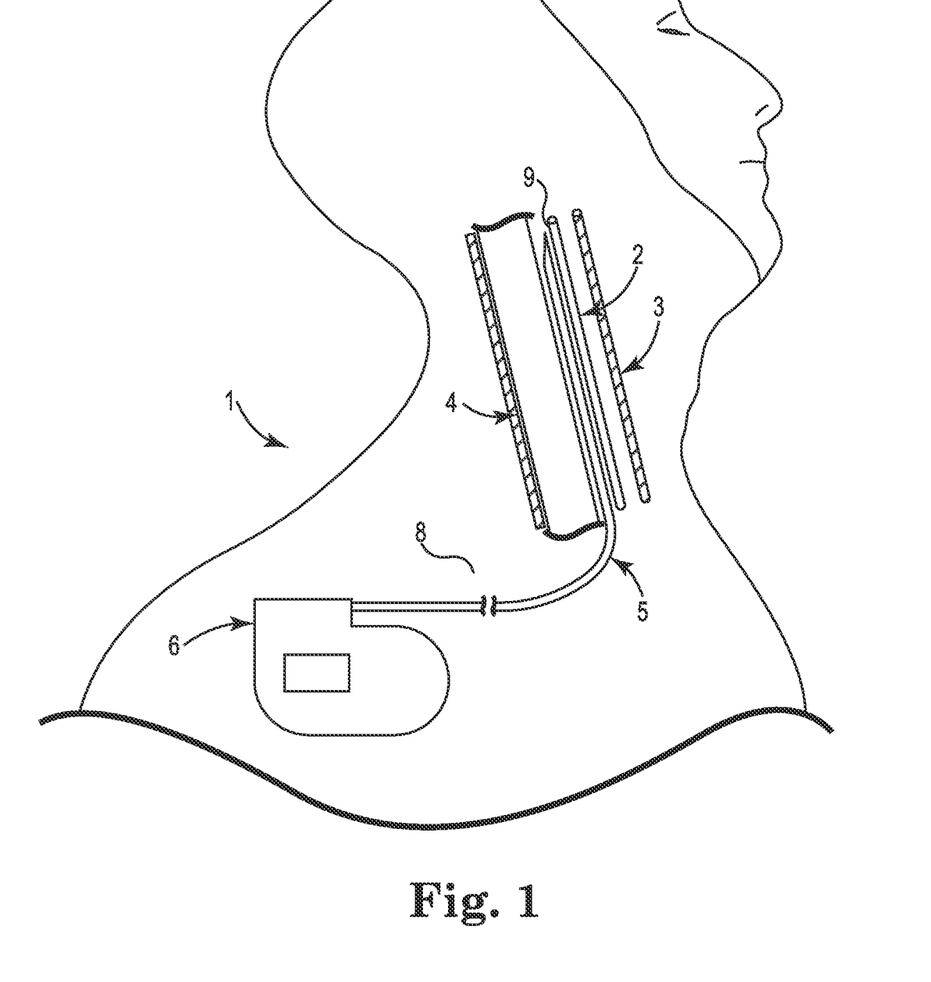
FIG. 1 is a schematic illustration showing a system for stimulating a region of a patient's vagus nerve located within a carotid sheath, according to some embodiments.

FIG. 1 is a schematic illustration showing a system 1 for stimulating a region of a patient's vagus nerve 2 located within a carotid sheath 3 (shown in cross-section in FIG. 1). As is known, the carotid sheath 3 consists of multiple layers of fascia in its interior, which wrap around the internal jugular vein (IJV) 4, the vagus nerve 2, and the carotid artery (shown in FIGS. 6-7). The carotid artery is adjacent both the IJV 4 and the vagus nerve 2 and is generally vulnerable to being punctured by sharp tips. Between the skin and carotid sheath 3 of a human body lies tissue 8, such as muscle tissue which is often susceptible to distortion in response to advancing or tunneling a blunt tool therethrough.

As shown, the system 1 includes a lead 5 and an implantable pulse generator 6. In the illustrated embodiment, the lead 5 is placed at a target site 9 for stimulation adjacent to and parallel to the vagus nerve 2, and the lead 5 is coupled to the pulse generator 6. In various embodiments, the system 1 can be used to selectively stimulate the vagus nerve 2 for treating cardiac disease. As such, in various embodiments, the lead 5 includes electrodes (not shown in FIG. 1) that are electrically and operatively coupled to electronics of the pulse generator 6 to deliver electrical stimuli to the vagus nerve 2 when implanted. In various embodiments, the lead 5 may be implanted in a minimally-invasive manner by subcutaneously tunneling a path between the implantation site of the pulse generator 6 and the target site 9 using delivery tools according to the various embodiments described herein. Such delivery tool embodiments can include, among other things, a novel needle assembly as described herein.

Figure 2:
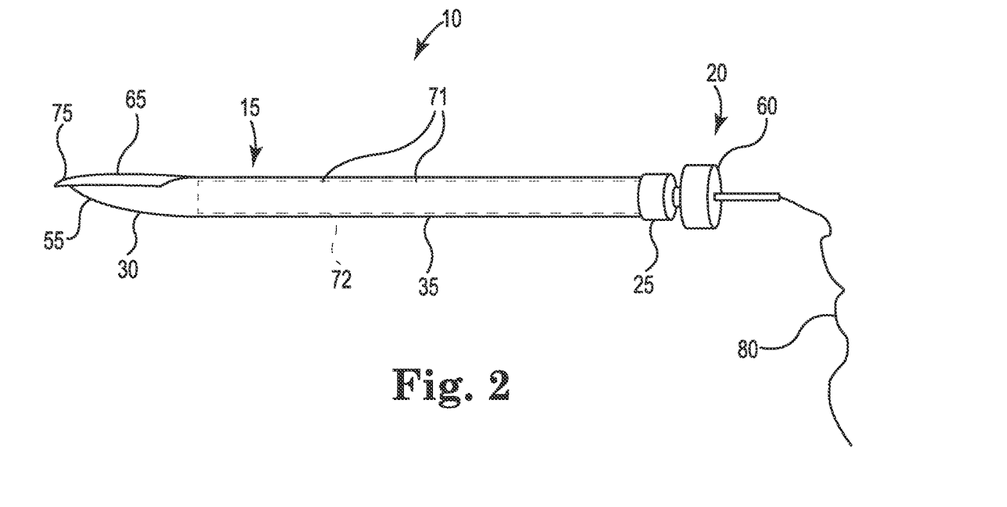
FIGS. 2 and 3 are, respectively, assembled and exploded perspective views of a needle assembly for use in tunneling to a target site for implantation of the lead of the stimulation system of FIG. 1, according to some embodiments.
Figure 3:
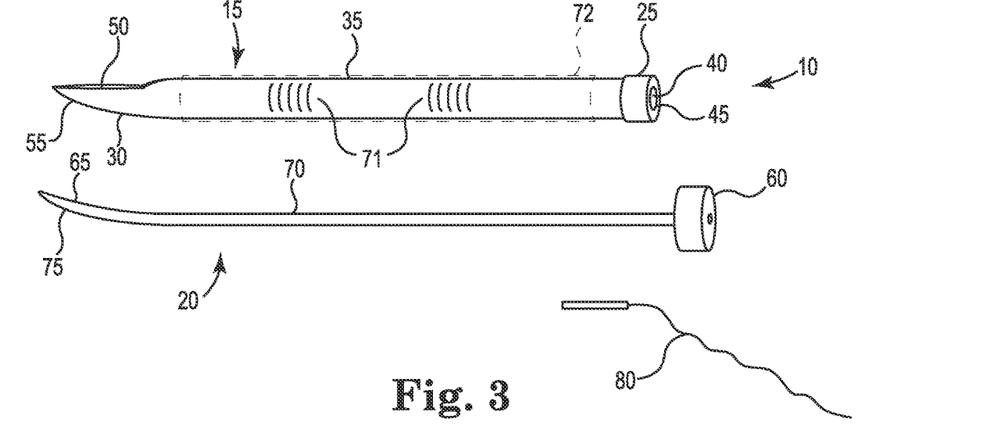

FIGS. 2 and 3 are, respectively, assembled and exploded perspective views of the needle assembly 10. As shown, the needle assembly 10 includes an outer needle 15 and an inner needle 20. In the various embodiments, as described in detail herein, the inner needle 20 and the outer needle 15 are configured so that the inner needle 15 can be protracted and retracted relative to the outer needle 15 during use. The inner needle 20 is configured to rotate relative to the outer needle 15. In response to the rotation, the inner needle 20 also protracts or retracts with respect to the outer needle 15 allowing the needle assembly 10 to be advanced through with a leading relatively sharp or relatively blunt tip, respectively, as described in more detail herein. In this way, the outer and inner needles 15, 20 cooperate such that the needle assembly 10 is adapted to selectively cut through tissue while also mitigating the potential for cutting vulnerable structures.

In the illustrated embodiment, the outer needle 15 includes a proximal end 25, a distal end 30, and a shaft 35 extending in a longitudinal direction between the proximal end 25 and the distal end 30. The shaft 35 is tubular and defines a lumen 40 that extends between a proximal opening 45 in the proximal end 25 of the outer needle 15 and a distal opening 50 in the distal end 30 of the outer needle 15. The lumen 40 has a diameter sized to slidably and rotatably receive the inner needle 20, as described in greater detail herein.

In various embodiments, the distal end 30 of the outer needle 15 and the portion of the lumen 40 disposed within the distal end 30 extend in a non-linear path relative to the shaft 35. In some embodiments, the distal end 30 and the portion of the lumen 40 disposed therein have a curved or angled profile relative to the shaft 35. One such embodiment of the outer needle 15 has a Tuohy needle configuration. In such embodiments, the distal opening 50 is oriented such that a device (such as a guidewire over which a stimulation lead may be delivered) exiting through the distal opening 50 will be urged outward at an oblique angle relative to the shaft 35.

In various embodiments, the distal end 30 of the outer needle 15 terminates at a distal tip 55. In various embodiments, the distal tip 55 has a relatively blunt profile and is sized and shaped, or otherwise adapted, to be advanceable through a narrow space in the body while reducing the potential for causing trauma to vulnerable structures. For example, the distal tip 55 may facilitate advancing tunneling the outer needle 15 through the interior space of the carotid sheath adjacent the IJV 4, the vagus nerve 2, and the carotid artery while minimizing the potential for perforating the carotid artery.

As further shown, the inner needle 20 includes a proximal end 60, a distal end 65, and a shaft 70 extending between the proximal end 60 and the distal end 65. In one embodiment, the inner needle 20 is sized to be slidably and rotatably received within the lumen 40 of the outer needle 15. In one embodiment, the inner needle 20 has a length selected such that the distal end 65 of the inner needle 20 can extend distally outward of the distal end 30 of the outer needle 15. In various embodiments, the distal end 65 of the inner needle 15 extends in a non-linear path relative to the shaft 70 of the inner needle 20.

In the illustrated embodiment, the distal end 65 of the inner needle 20 is curved. In one embodiment, the inner needle 20 may have a curvature sized and shaped to nest in the curvature within the lumen 40 of the outer needle 15.

In one embodiment, the distal end 65 may form a reverse curve distal to the distal end 30 of the outer needle 15. In some embodiments, the reverse curve operates to releasably lock the inner needle 20 in place in a protracted position with respect to the outer needle 15, as further explained herein.

In various embodiments, the distal end 65 of the inner needle 20 terminates in a distal tip 75. In one embodiment, the distal tip 75 has a relatively sharp profile and is sized and shaped, or otherwise adapted, to facilitate advancement of the inner needle 20 through tissue in the body by cutting or dissecting the tissue while reducing the physical distortion of the tissue. For example, the distal tip 75 comprises one of a point, a bevel tip (i.e., a bevel at the tip), and a bevel edge extending along a length of the inner needle (i.e., similar to a knife edge).

Reducing the distortion of the tissue can reduce unintended tissue damage and improve accuracy of imaging systems used while tunneling. For example, the distal tip 75 may advance, or tunnel, through tissue 8 between the skin and the target site 9 while reducing distortion of the tissue for ultrasound imaging. The result improves the chances of accurate delivery with less damage to the body.

As illustrated, in the assembled needle assembly 10, the inner needle 20 is disposed, at least partially, within the outer needle 15. The inner needle 20, for example, may be inserted into and removed through the proximal opening 45 of the outer needle 15. In some embodiments, the inner needle 20 and outer needle 15 form a relatively close internal fit, effectively defining a seal to substantially prevent tissue from being taken into the lumen 40 of the outer needle 15 while at the same time facilitating relative rotational and translational movement between the inner needle 20 and the outer needle 15.

The sizes of the outer needle 15 and the inner needle 20 can be chosen depending on the particular clinical needs in which the needle assembly 10 is used. In some embodiments, the outer needle 15 can have a size ranging from 14 gauge to 20 gauge, though other appropriate sizes may be selected by one having skill in the art.

In one embodiment, the inner needle 20 and the lumen 40 of the outer needle 15 have diameters sized so that the inner needle 20 can slidably contact an inner surface of the lumen 40 when the inner needle 20 is disposed within the lumen 40.

The outer and inner needles 15, 20 may be made of any suitable biocompatible material(s) having an appropriate rigidity for cutting tissue and withstanding manual rotational forces. In some embodiments, the outer needle 15 can be made of an electrically conductive material. Similarly, in some embodiments, the inner needle 20 can be made of an electrically conductive material, which may be the same material or a different material used for the outer needle 15.

In various embodiments utilizing electrically conductive outer and inner needles 15, 20, the needle assembly 10 includes a conductive wire 80 electrically coupled to one or both of the outer and inner needles 15, 20. In the illustrated embodiment, the conductive wire 80 is electrically and mechanically coupled to the proximal end 60 of the inner needle 20. The conductive wire 80 may be used to deliver an electrical test charge to the inner needle 20. When the inner needle 20 is positioned within the lumen 40 of the outer needle 15 such that the distal ends 30, 65 of the outer and inner needles 15, 20 are in contact with one another, the electrical test charge may be conducted through the inner needle 20 to the distal end 30 of the outer needle 15. As such, the needle assembly 10 is adapted to deliver an electrical test charge to the environment adjacent the distal end 30 of the outer needle 15. This can be useful, for example, to test whether the needle assembly 10 is positioned adjacent an intended target site 9.

In various embodiments, needle assembly 10 includes an insulator 72 disposed on the outer needle 15 proximal to the distal end 30. The insulator 72 electrically isolates the environment adjacent the shaft 35 of the outer needle from an electrical test charge while leaving the distal end 30 exposed. Insulator 72 may be made of any suitable biocompatible material with insulating electrical properties.

In some embodiments, the needle assembly 10 includes one or more echogenic features 71, which facilitate observation of the needle assembly under ultrasound imaging, for example, using an ultrasound probe.

The needle assembly 10 is configured such that the inner needle 20 can transition between retracted and protracted positions relative to the outer needle 15. When in the protracted position, the distal tip 75 of the inner needle 20 facilitates cutting through tissue as the needle assembly 10 is advanced through the tissue. When in the retracted position, the distal tip 75 of the inner needle is nested or recessed within the distal end 30 of the outer needle 15, so that tissue adjacent the needle assembly 10 is not exposed to the distal tip 75. In this way, the needle assembly 10 may be advanced within or through the tissue while minimizing the potential for cutting or dissecting the tissue by the sharp distal tip 75.

In one embodiment, as explained elsewhere, the relative diameters of the inner needle 20 and the lumen 40 may be selected so as to result in a close fit between the inner needle 20 and the inner surface of the lumen 40. In such an embodiment, this close fit operates to inhibit coring tissue as the needle assembly 10 is advanced through tissue with the inner needle 20 in the protracted position.

Figure 4:
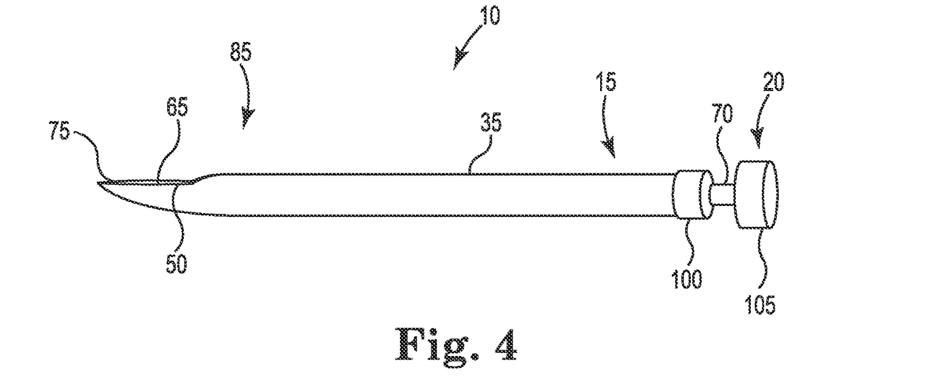
FIGS. 4 and 5 are perspective views of the needle assembly of FIGS. 2 and 3 showing, respectively, an inner needle thereof in a retracted position and a protracted position according to some embodiments.
Figure 5:
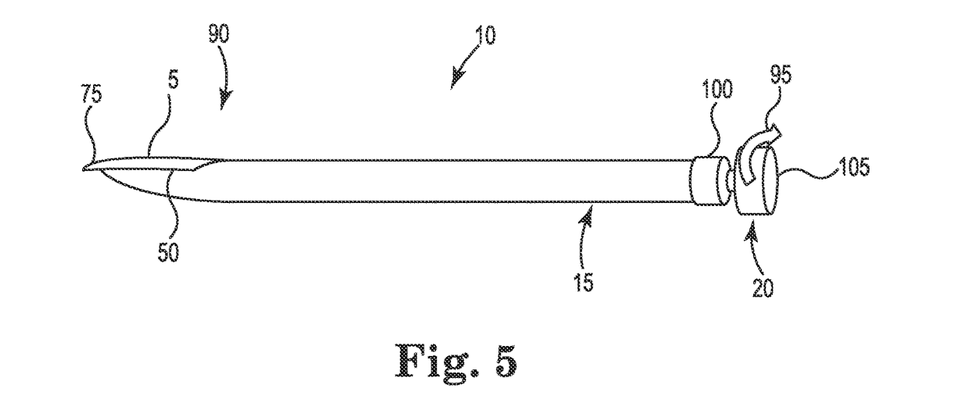

FIGS. 4 and 5 are perspective views of the needle assembly 10 showing, respectively, the inner needle 20 in a retracted position 85 and a protracted position 90 according to some embodiments. As shown, when the inner needle 20 is in the retracted position 85, the distal tip 75 of the inner needle 20 is retracted into the outer needle 15 such that it is located proximal to the distal tip 55 of the outer needle 15. The inner needle 20 may also fill the lumen 40 when retracted into the outer needle 15. As shown in FIG. 5, when the inner needle 20 is in the protracted position 90, the distal tip 75 of the inner needle 20 is protracted relative to the distal tip 55 of the outer needle 15.

In some embodiments, the needle assembly 10 can be configured such that the inner needle 20 transitions from its retracted position 85 to the protracted position 90 in response to a rotation 95 of the inner needle 20 relative to the outer needle 15. In some embodiments, the curved or angled shape of the distal end 65 of the inner needle 20 is configured such that upon rotation of the inner needle 20 relative to the outer needle 15, the distal end 65 cooperates with the curved or angled distal end 30 of the outer needle 15 to urge the inner needle 20 longitudinally with respect to the outer needle 15, such that the distal tip 75 of the inner needle 20 extends through the distal opening 50 of the outer needle 15 by a pre-determined length.

In other embodiments, the rotation 95 facilitates freeing the inner needle 20 from the nested, retracted position 85 so that it can be manually protracted, or pushed into the protracted position 90.

In yet other embodiments, the needle assembly 10 includes one or more threads (e.g., shown in FIGS. 6B-6C) disposed between the outer and inner needle 15, 20 configured to guide the relationship between the rotational travel (e.g., clockwise and counter-clockwise) and the longitudinal travel (i.e., protraction or retraction) of the inner needle with respect to the outer needle 15.

In various embodiments, a rotation of the inner needle 20 in one direction relative to the outer needle 15 will protract the inner needle 20 while a rotation of the inner needle 20 in another, opposite direction will retract the inner needle 20 with respect to the outer needle 15.

In some embodiments, when in the protracted position 90, the curved or angled shape of distal end 65 of the inner needle 20 is configured such that the outer surface of the distal end 65 bears against the distal tip 55 of the outer needle 15 to resist forces on the inner needle 20 that would otherwise urge the inner needle 20 back into the outer needle 15. That is, the shape of the distal end 65 of the inner needle 20 is configured so as to inhibit the inner needle 20 from reverting to its retracted position 85 when the protracted position 90 is desired.

Various embodiments of the needle assembly 10 include one or more handles for enhancing handling of the needle assembly 10, in particular the outer needle 15 and the inner needle 20. As shown, the outer needle 15 includes optional handle 100. Also shown, inner needle 20 includes optional handle 105. Each handle 100, 115 has a lateral width greater than the lateral width of the respective shaft 35, 70. However, handles 100, 105 may be sized and shaped in any manner suitable for accommodating manual handling. Additionally or alternatively, handles 100, 105 include a texture to enhance the frictional interference and therefore the handling of the needles 15, 20.

In some embodiments, the handles 100, 105 are configured prevent the inner needle 20 from extending beyond the protracted position. For example, the handle 100 of the outer needle 15 can be configured to bear against the handle 105 of the inner needle 20 so as to prevent distal movement of handle 105 relative to the outer needle 15, and consequently resist extension of the inner needle 15 beyond a predetermined distance. In other embodiments, the handles 100, 105 do not limit the extension of the inner needle 20 in this manner.

Figure 6A:
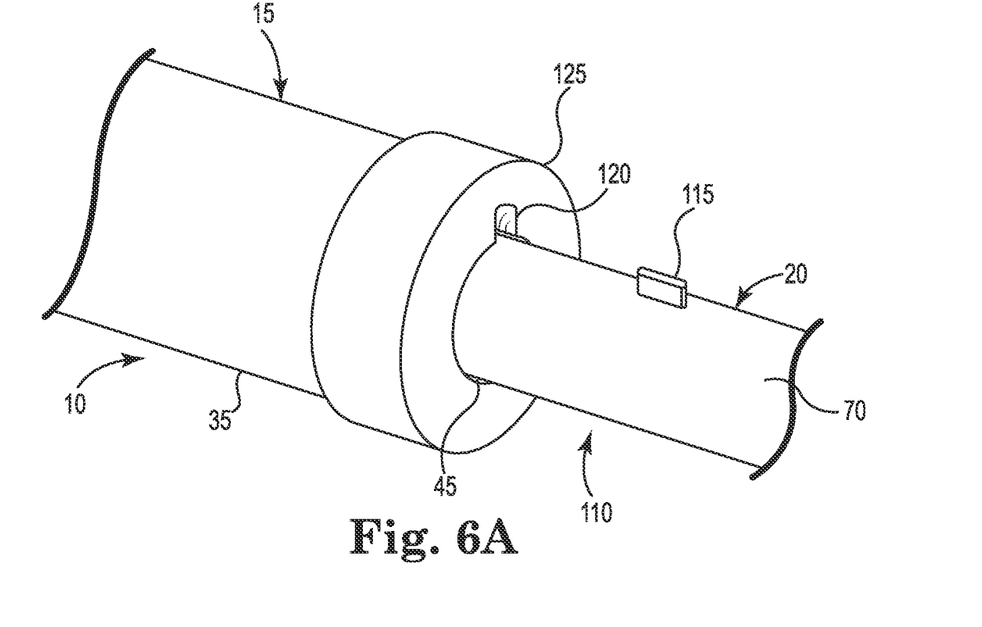
FIGS. 6A-6C are schematic illustrations of portions of the needle assembly of FIGS. 2 and 3 showing a stopping feature for regulating the protraction and retraction of the inner needle thereof, according to some embodiments.
Figure 6B:
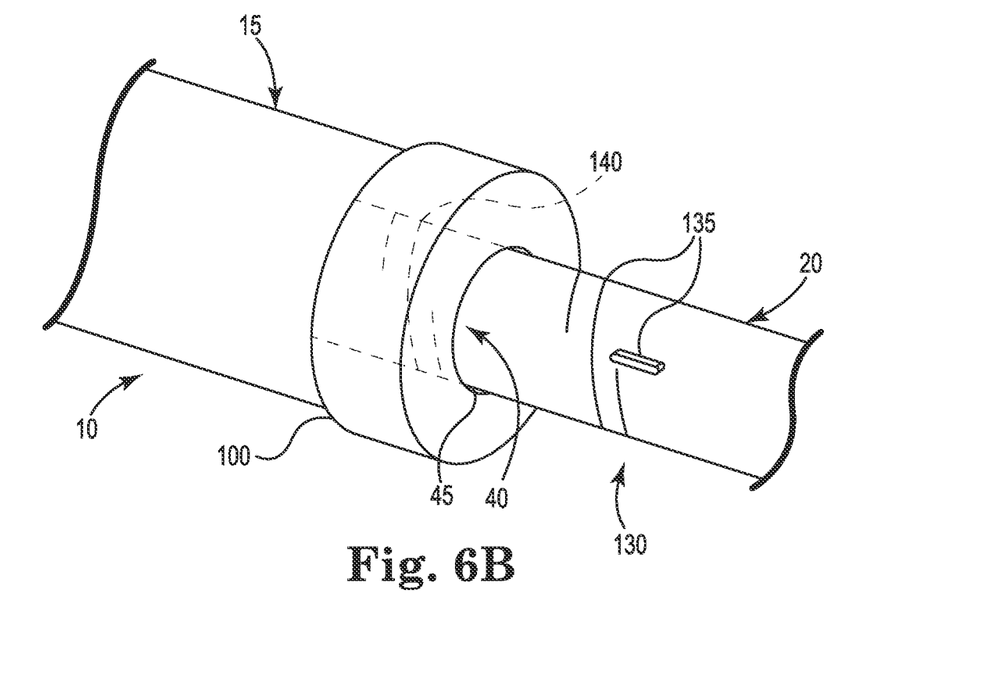
Figure 6C:
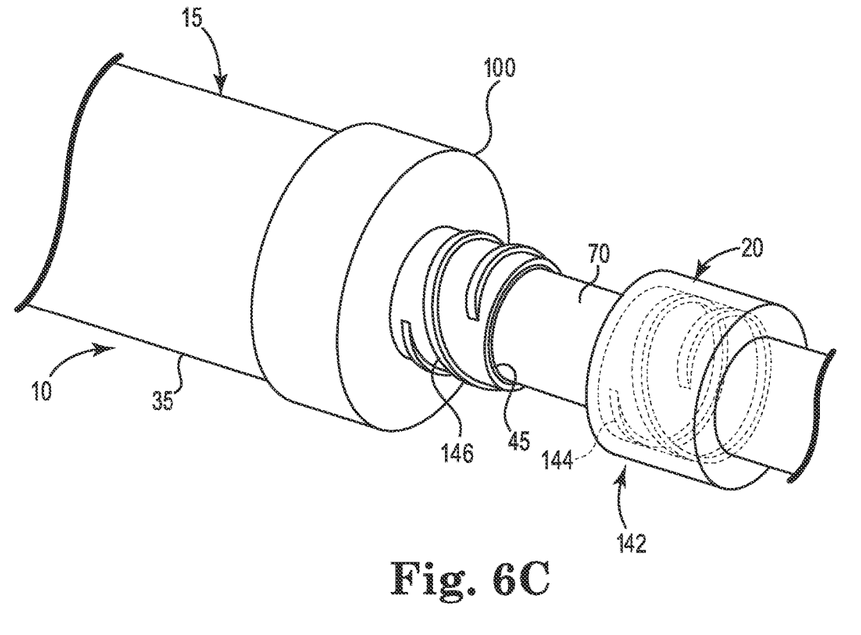

FIGS. 6A-C are perspective views of a portion of an alternative embodiment of the needle assembly 10 including optional stopping features operable to regulate the movement of the inner needle 20 relative to the outer needle 15.

As shown, the shaft 70 of the inner needle 20 extends through proximal opening 45 of the outer needle 15. The stopping feature prevents, for example, the inner needle 20 from extending beyond a targeted distance for the protracted position 90. For example, various embodiments of the stopping feature are configured to releasably lock the inner needle 20 in the retracted position 85 or the protracted position 90. In some embodiments, the stopping feature is configured to resist the longitudinal travel of the inner needle 20 with respect to the outer needle 15. In further embodiments, the stopping feature is configured to limit the rotational travel of the inner needle 20 with respect to the outer needle 15.

Shown in FIG. 6A is a stopping feature 110 comprising a protrusion 115 and a recess 120, according to some embodiments. In the illustrated embodiment, the protrusion 115 is on the inner needle 20 and the recess 120 is on a handle 125 of the outer needle 15. In other embodiments, the protrusion 115 can be on the outer needle 15 and the recess 120 can be on the inner needle 20. In various embodiments, the needle assembly 10 can include two or more protrusions 115 and corresponding recesses 120.

In one embodiment, the protrusion 115 is sized so as to have a height greater than the clearance between the outer surface of the inner needle shaft 70 and the inner surface of the outer needle shaft 35 when the inner needle 20 is disposed within the lumen 40 of the outer needle 15. The protrusion 115 is positioned on the inner needle 20 to delimit longitudinal travel of the inner needle 20 within the outer needle lumen 40 so as to prevent the protraction of the inner needle 20 beyond a predetermined distance. In some embodiments, the predetermined distance for extension of the distal tip 75 of the inner needle 20 beyond the outer needle 15 can range from about 1 millimeter to about 10 millimeters. In one embodiment, this predetermined distance is about 3 millimeters. In various embodiments, other ranges for this predetermined distance can be selected based on the particular clinical needs for the needle assembly 10.

As further shown in FIG. 6A, the recess 120 is formed on a proximal face of the handle 125 of the outer needle 15. In the illustrated embodiment, the protrusion 115 is configured to fit into the recess 120 to prevent rotation of the inner needle 20 relative to the outer needle 15. In addition, recess 120 has stop surface (not shown in FIG. 6A) against which the distal surface of the protrusion 115 bears when fully seated in the recess 120, which operates to limit longitudinal extension of the inner needle 20 within the lumen 40 of the outer needle 15. In such embodiments, the predetermined distance for protraction of the inner needle distal tip 75 beyond the distal tip 65 of the outer needle 15 is in part defined by the depth of the recess 120.

In varied embodiments (not shown), the recess 120 is configured as an arc, allowing the protrusion 115 to rotate along a predetermined circumferential distance while received within the recess 120. For example, the arc-shaped recess 120 may allow the inner needle to rotate 180 degrees with the protrusion 115 received therein.

In the embodiment of the needle assembly 10 shown in FIG. 6B, the needle assembly 10 includes an additional stopping feature 130 comprising an external thread 135 on the outer surface of the inner needle 20, and an internal thread 140 on the inner surface of the lumen 40 of the outer needle 15. Aside from the thread arrangement described herein, the outer needle 15 and inner needle 20 can be otherwise similar or identical to those shown in and described with respect to FIG. 6A.

In the particular illustrated embodiment, the thread 140 is within lumen 40 of the outer needle 15. The threads 135, 140 are configured to engage each other so that relative rotation of the inner needle 20 and the outer needle 15 causes the inner needle 15 to translate longitudinally relative to the outer needle 15. Consequently, the threads 135, 140 guide the rotation and extension of the inner needle 20 with respect to the outer needle 15. As will be appreciated based on the foregoing, the axial extent of the threads 135, 140 will define the extent of longitudinal translation of the inner needle 20 relative to the outer needle 15. In addition, upon complete rotation of the inner needle 20 relative to the outer needle 15 so that the distal ends of the respective threads 135, 140 meet, further rotation in the same direction will be prevented. In this way, the threads 135, 140 operate to delimit both longitudinal and rotational movement of the inner needle 20 relative to the outer needle 15.

In the illustrated embodiment, the inner needle 15 may include a backstop or protrusion at the proximal end of the thread 135. The protrusion prevents further extension of the inner needle 20 with respect to the outer needle 15, for example, when handle 100 interferes with the movement of the protrusion. In various embodiments, the protrusion on the thread 135 may be similar in shape and size to protrusion 115.

FIG. 6C shows yet another embodiment of a stopping feature 142 comprising a Luer fitting. In the illustrated embodiment, the Luer fitting includes a female portion having internal threads 144 and a male portion having external threads 146. The threads 144, 146 may be configured to cooperate together in a manner similar to threads 135, 140 to regulate movement of the inner needle 20 with respect to the outer needle 15. Moreover, the female portion of the Luer fitting may be configured as a Luer cap having an open side and a closed side on opposing axial ends of the female portion. The Luer cap further regulates the distal, or axial, movement of the inner needle 20 with respect to the outer needle 15 when the male portion is inserted through the Luer cap to the point of engaging the closed side of Luer cap.

As further illustrated, the male portion of the Luer fitting is disposed on the outer needle 15. In particular, the male portion extends proximally from the face of the outer needle handle 100. The male portion may be integrally formed in the outer needle handle 100. The male portion may include an aperture. For example, the proximal opening 45 is formed in the male portion. The inner needle shaft 70 may be inserted into the proximal opening 45. In such embodiments, the female portion may be disposed on the inner needle shaft 70. The female portion of the Luer fitting may engage the outer needle handle 100 to further regulate the distal, or axial, movement of the inner needle 20 with respect of the outer needle 15. In further embodiments, the female portion may be integrally formed in the inner needle handle 105 (not shown here). In yet further embodiments, the female portion of the Luer fitting may be disposed on the outer needle 15, and the male portion of the Luer fitting may be disposed on the inner needle 20.

Figure 7:
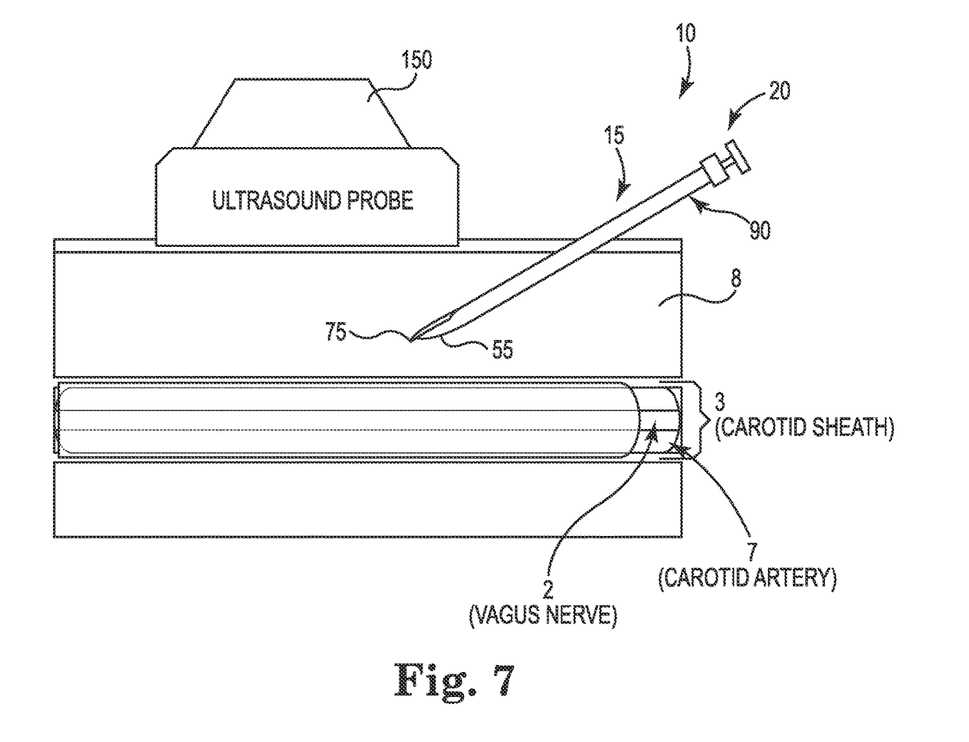
FIGS. 7 and 8 are schematic illustrations of the needle assembly of FIGS. 2 and 3 in use within tissue of a patient, according to some embodiments.
Figure 8:
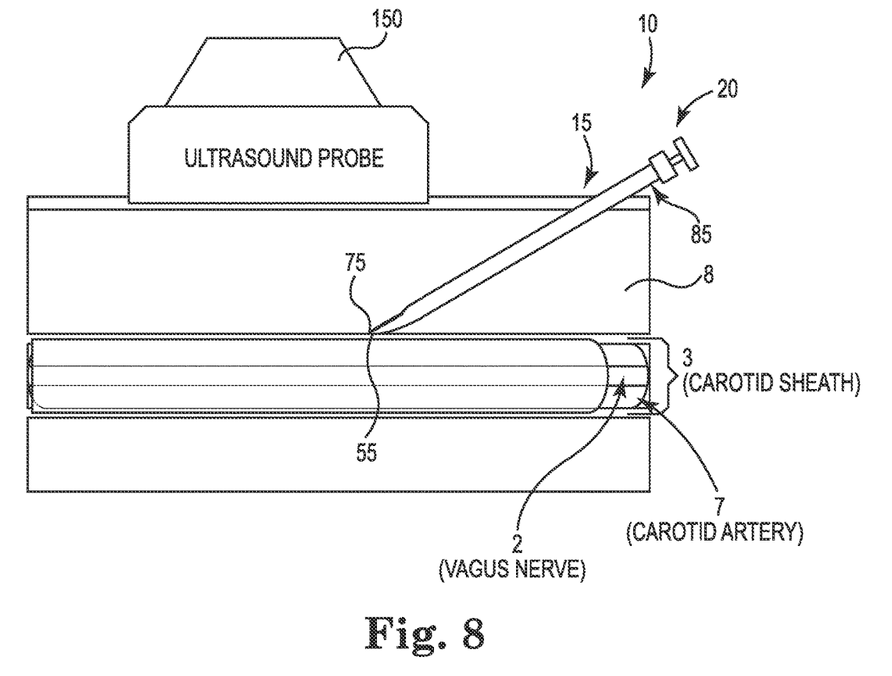

FIGS. 7 and 8 show schematic examples of the needle assembly 10 in use, according to some embodiments. FIG. 7 shows a schematic example of the needle assembly 10 advancing through tissue toward a target site before approaching a bodily structure. FIG. 8 shows a schematic example of the needle assembly 10 advancing through tissue after approaching a bodily structure.

The carotid sheath 3, as shown, surrounds a portion of the vagus nerve 2, carotid artery 7, and IJV (shown in FIG. 1). Ultrasound probe 150 is placed adjacent the patient's skin to provide an ultrasound image to a user of the needle assembly 10, which helps guide it through the tissue 8. While the needle assembly 10 advances through tissue 8 under ultrasound guidance, the distal tip 75 of the inner needle 20 is protracted and extends beyond the tip 55 of the outer needle 15. The distal tip 75 facilitates cutting through the tissue 8 when so positioned as the needle assembly 10 tunnels through the tissue 8.

Through imaging, provided by the ultrasound probe 150 or an ultrasound transducer (not shown) on the needle assembly 10, the user may determine the proximity of the needle assembly 10 to a bodily structure, such as the carotid sheath 3. When close, the user may retract the distal tip 75 into the tip 55 of the outer needle 15. The tip 55 then acts as the leading point of the needle assembly 10, as shown in FIG. 8, with the inner needle 20 in the retracted position 85.

When the inner needle 20 is in the retracted position, the needle assembly 10 may advance into the carotid sheath 3 and tunnel along a space within the carotid sheath adjacent the vagus nerve 2. With the tip 55 of the outer needle 15 leading and the distal tip 75 of the inner needle 20 retracted into the tip 55, the potential for unintended trauma to surrounding tissues is reduced.

Figure 9:
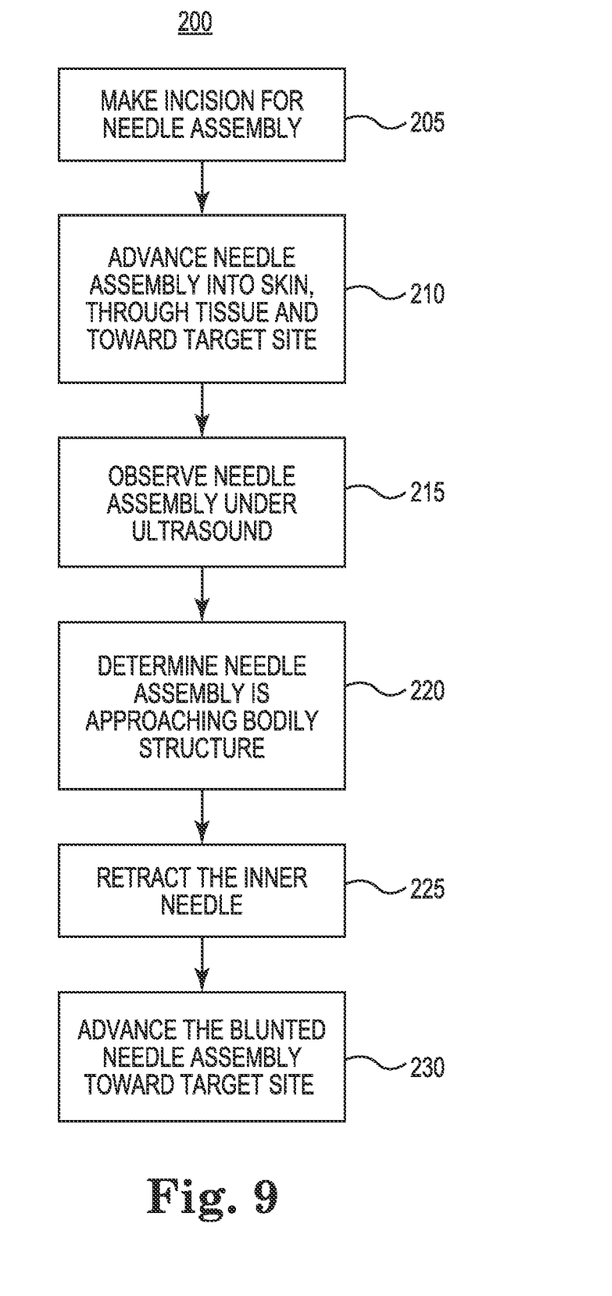
FIG. 9 shows an exemplary method of using the needle assembly of FIG. 2 to tunnel toward a target site, according to some embodiments.

FIG. 9 shows an exemplary method 200 of using the needle assembly of FIG. 2 to tunnel toward a target site, according to some embodiments. In step 205, an incision is made to allow a needle assembly to enter the skin. In step 210, the needle assembly is advanced into the skin, through some tissue, and toward a target site. As the needle assembly is advanced, a passage is created through the body. The target site may be a target site for stimulation or other sites requiring tunneling near structures vulnerable to puncture by a sharp tip.

In step 215, the needle assembly is observed under ultrasound, for example, by imaging through an external probe or a transducer on the needle assembly. In step 220, a determination is made that the needle assembly is approaching a bodily structure, such as the carotid sheath or other structure. The determination indicates that the same or another structure vulnerable to puncture is near the tip of the needle assembly in some embodiments.

In step 225, the inner needle of the needle assembly is retracted relative to the outer needle. In some embodiments, the inner needle is rotated relative to the outer needle concurrently with the retracting. The retraction of the inner needle causes the tip of the inner needle to move into the tip of the outer needle to reduce the potential for cutting the structure. In step 230, the needle assembly is advanced toward a target site with the inner needle in the retracted position.

In other embodiments, the inner needle of the needle assembly may be retracted in steps 205, 210, 215, and 220 in view of vulnerable anatomical structures being present near the tip of the needle assembly. In step 225, the rotation causes the sharp tip of the inner needle to protract from the blunt tip of the outer needle so that the needle assembly facilitates cutting tissue. In step 230, the needle assembly is advanced toward a target site in protracted form.

Figure 10:
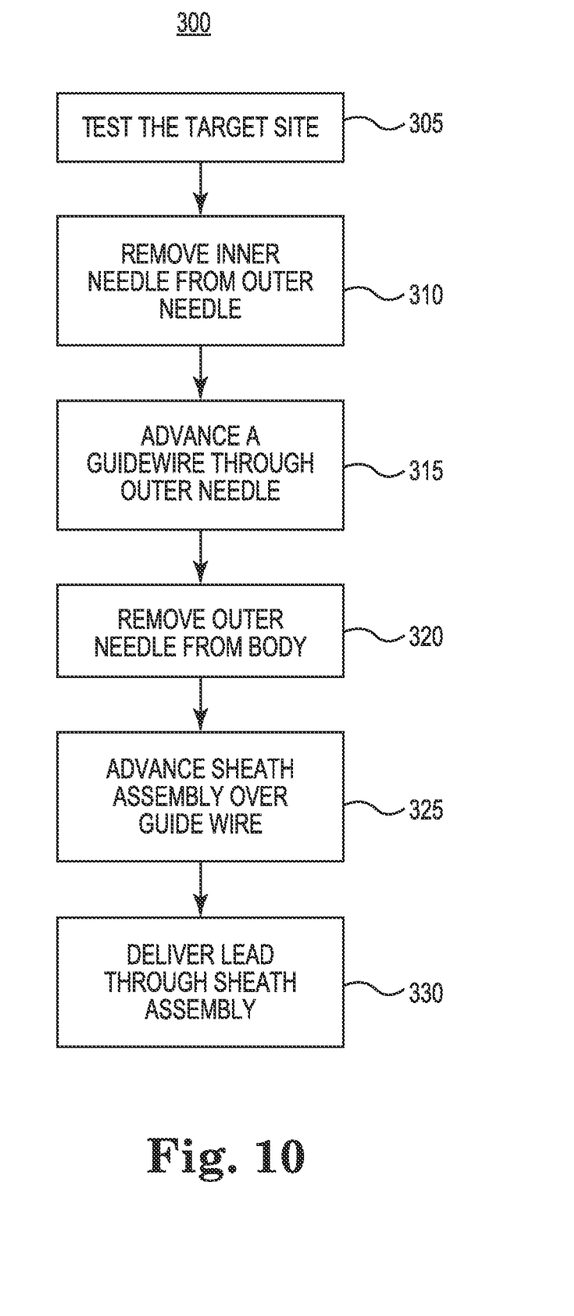
FIG. 10 shows an exemplary method of using the needle assembly of FIG. 2 to deliver a lead to a target site after tunneling, according to some embodiments.

FIG. 10 shows an exemplary method 300 of using the needle assembly of FIG. 2 to deliver a lead to a target site after tunneling, according to some embodiments. Method 300 may follow method 200 to deliver the lead to the target site. In step 305, the target site is tested. In some embodiments, an electrical test charge may be delivered from a pulse generator to a conductive wire to an inner needle to the tip of an outer needle and finally to the environment adjacent the tip of the outer needle. Then, a bodily reaction is observed to determine whether the needle assembly is acceptably placed relative to the target site. If the target site is not acceptable, then the needle assembly is repositioned and optionally tested again. If the target site is acceptable, then step 310 is performed.

In step 310, the inner needle is removed from the outer needle. This creates a space for a guidewire to occupy in the outer needle. In step 315, a guidewire is advanced through the outer needle after passing through a passage created by the needle assembly. The tip of the guidewire is generally placed adjacent the target site. Placement of the guidewire may be aided by using a curved or angled profile on the outer needle distal end, such as a Tuohy needle configuration. An optional test may be performed through an electrode on the tip of the guidewire to test placement of the guidewire, similar to step 305, but using the tip of the guidewire instead of the tip of the outer needle.

In step 320, the outer needle is removed from the body. The guidewire is left in place adjacent the target site. In step 325, a sheath assembly is advanced over the guidewire. The sheath assembly generally creates a larger passage, or dilates the passage, to provide space for a lead to be advanced.

In step 330, a lead is delivered through the sheath assembly after passing through the dilated passage over the guide wire. In some embodiments, the guidewire and the sheath are subsequently removed from the body, leaving the lead in place.

The assembly and methods described provide means for effective yet less invasive introduction of a lead to the body. Through some embodiments disclosed relate to delivering a lead to the vagus nerve, other uses of the needle assembly 10 are contemplated which may benefit from cutting tissue and reducing the potential for cutting vulnerable structures. For example, the needle assembly 10 may be used to deliver a lead near the epicardium, the subxiphoid pericardium, and any peripheral nerve, vein, or bodily structure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A needle assembly comprising:
   an outer needle including a proximal end having a proximal opening, a distal end having a distal opening, a shaft defining a lumen extending between the proximal opening and the distal opening, and a tip on the distal end, the distal end being curved relative to the shaft; and
   an inner needle including a proximal end, a distal end, a shaft extending between the proximal end and the distal end, and a tip on the distal end adapted to cut tissue, the distal end being curved relative to the shaft, the inner needle removably received into the lumen,
   wherein the needle assembly is configured to be transitioned between a protracted position and a retracted position, and wherein in the protracted position, the tip of the inner needle extends outwardly from the distal opening of the outer needle in a reverse curve from the curve of the distal end of the outer needle to facilitate cutting tissue, and in the retracted position, the tip of the inner needle is positioned within the distal opening of the outer needle so that the tip of the inner needle is not directly exposed to tissue as the needle assembly is advanced therethrough in use, and
   wherein the curvatures of the distal ends of the inner and outer needles are configured so that the distal end of the outer needle receives the distal end of the inner needle in a nesting fit when the inner needle is in the retracted position, the distal end of the inner needle forms the reverse curve distal to the distal end of the outer needle when the inner needle is in the protracted position, and are configured further so that the inner needle transitions from the retracted position to the protracted position in response to a first rotation relative to the outer needle.

2. The needle assembly of claim 1, wherein the needle assembly is configured such that the inner needle transitions from the protracted position to the retracted position in response to a second rotation relative to the outer needle, and wherein the tip of the inner needle has a first orientation in the retracted position and a second orientation, which is opposite the first orientation, in the protracted position.

3. The needle assembly of claim 1, wherein the inner needle is configured to be releasably locked in the protracted position.

4. The needle assembly of claim 3, wherein the distal ends of the inner and outer needles have complementary curvatures configured to cooperate so that the distal end of the inner needle bears against the distal tip of the outer needle so as to releasably retain the inner needle in the protracted position.

5. The needle assembly of claim 4, further including one or more threads disposed on the outer needle and the inner needle configured to cooperatively guide the movement of the inner needle between the protracted position and the retracted position upon relative rotation of the inner and outer needles.

6. The needle assembly of claim 4, further including a first stopping feature on one or both of the outer needle and the inner needle configured to inhibit extension of the inner needle beyond the protracted position.

7. The needle assembly of claim 6, further including a second stopping feature configured to inhibit rotation of the inner needle relative to the outer needle beyond the second orientation.

8. The needle assembly of claim 1, wherein the inner needle and the lumen of the outer needle have diameters sized so that the inner needle can slidably contact an inner surface of the lumen when the inner needle is disposed within the lumen.

9. The needle assembly of claim 8, wherein the inner needle and the outer needle are each at least partially made of an electrically conductive material, and wherein the distal end of the outer needle is electrically coupled to the proximal end of the inner needle through contact between the electrically conductive material of the inner needle and the electrically conductive material of an inner surface of the lumen of the outer needle, and further including a conductive wire electrically coupled to the proximal end of the inner needle for conducting an electrical stimulation pulse to the inner needle.

10. The needle assembly of claim 9, further including an insulator on the outer surface of the shaft of the outer needle proximal to the distal end thereof.

11. The needle assembly of claim 10, wherein the inner needle and the lumen of the outer needle are sized to provide a seal to inhibit take up of tissue into the lumen of the outer needle as the needle assembly is advanced through the tissue while at the same time facilitating relative rotational and translational movement between the inner needle and the outer needle.

12. A needle assembly comprising:
- an outer needle including a proximal end having a proximal opening, a distal end having a distal opening, a shaft defining a lumen extending between the proximal opening and the distal opening, and a tip on the distal end, the distal end extending in a non-linear path relative to the shaft; and
- an inner needle including a proximal end, a distal end, a shaft extending between the proximal end and the distal end, and a tip on the distal end adapted to cut tissue, the distal end extending in a non-linear path relative to the shaft, the inner needle removably received into the lumen,
- wherein the needle assembly is configured to be transitioned between a protracted position and a retracted position, and wherein in the protracted position, the tip of the inner needle extends outwardly from the distal opening of the outer needle in a reverse curve from the curve of the distal end of the outer needle to facilitate cutting tissue, and in the retracted position, the tip of the inner needle is positioned within the distal opening of the outer needle so that the tip of the inner needle is not directly exposed to tissue as the needle assembly is advanced therethrough in use, and
- wherein the shapes of the distal ends of the inner and outer needles are configured so that the distal end of the outer needle receives the distal end of the inner needle in a nesting fit when the inner needle is in the retracted position, the distal end of the inner needle forms the reverse curve distal to the distal end of the outer needle when the inner needle is in the protracted position, and are configured further so that the inner needle transitions from the retracted position to the protracted position in response to a first rotation relative to the outer needle.

13. The needle assembly of claim 12, wherein the inner needle is configured to be releasably locked in the protracted position so that the distal end of the inner needle bears against the distal tip of the outer needle, and wherein the needle assembly is further configured so that the inner needle transitions from the protracted position to the retracted position in response to a second rotation relative to the outer needle.

* * * * *